United States Patent [19]
Ouchi et al.

[11] Patent Number: 5,947,979
[45] Date of Patent: Sep. 7, 1999

[54] WIRE LOOP TYPE INSTRUMENT FOR ENDOSCOPE AND METHOD OF PRODUCING THE SAME

[75] Inventors: Teruo Ouchi, Saitama; Miyuki Nishimura, Nagano, both of Japan

[73] Assignee: Asahi Kogaku Kogyo Kabushiki Kaisha, Tokyo, Japan

[21] Appl. No.: 09/124,080

[22] Filed: Jul. 29, 1998

[30]    Foreign Application Priority Data

Aug. 7, 1997  [JP]  Japan ................................. P9-212776
Oct. 1, 1997  [JP]  Japan ................................. P9-268293

[51] Int. Cl.$^6$ .................................................. A61B 17/32
[52] U.S. Cl. ............................................ 606/113; 606/47
[58] Field of Search .................................. 606/113, 127, 606/128, 47

[56]    References Cited

U.S. PATENT DOCUMENTS 4,633,871  1/1987  Shinozuka .
5,752,961  5/1998  Hill ......................................... 606/113

FOREIGN PATENT DOCUMENTS 5-176941   7/1993   Japan .
6-98143   12/1994   Japan .

OTHER PUBLICATIONS

Copy of an English Language Abstract of JP No. 5–176941.

*Primary Examiner*—Michael H. Thaler
*Attorney, Agent, or Firm*—Greenblum & Bernstein, P.L.C.

[57]    ABSTRACT

A wire loop type instrument for an endoscope that uses an elastic wire formed from a stranded wire bent into a U-shape and looped at the rear of the U-shaped bent portion. Each strand of the stranded wire has a non-circular cross-sectional configuration in which the strand is more resistant to bending in other directions than in a direction toward the center of the elastic wire. The stranded wire is formed by twisting together a plurality of strands each having a circular cross-section. The stranded wire is passed through a die with a hole having a smaller diameter than that of the stranded wire, thereby compression-deforming each strand into a non-circular cross-sectional configuration. A composite stranded wire may be used as the elastic wire, which is formed by twisting together a plurality of stranded wires each formed from a plurality of strands twisted together.

4 Claims, 6 Drawing Sheets

FIG.7   7×3
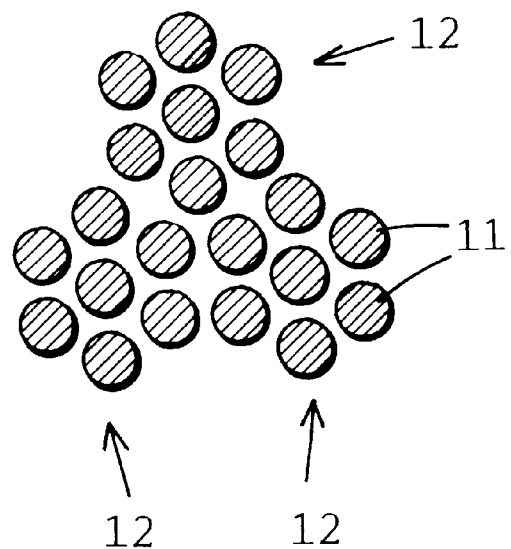
FIG.8   7×7
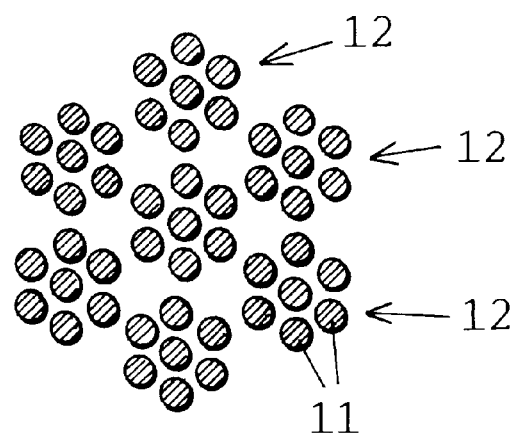

FIG.9   (1×3)+(1×7)×5
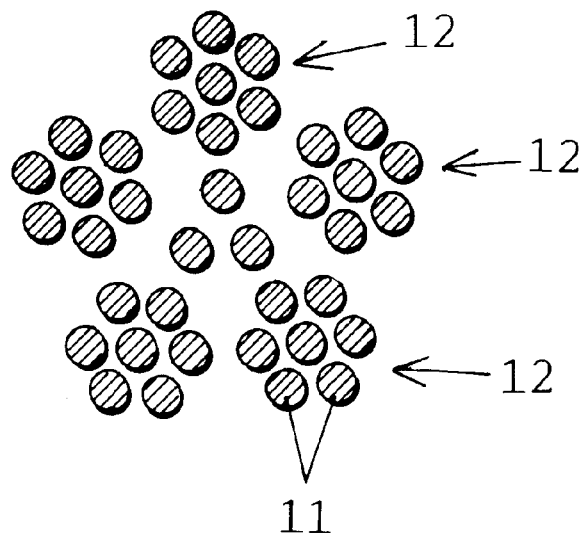
FIG.10   PRIOR ART
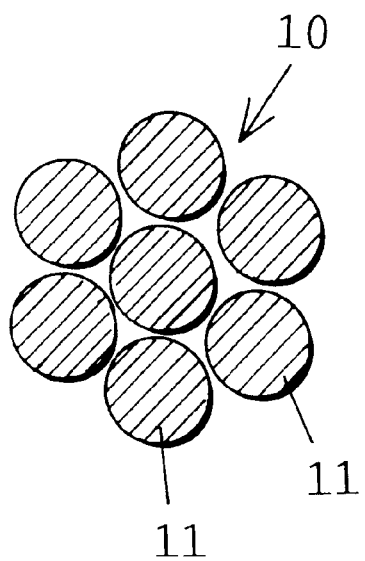

WIRE LOOP TYPE INSTRUMENT FOR ENDOSCOPE AND METHOD OF PRODUCING THE SAME

BACKGROUND OF THE INVENTION

The present disclosure relates to subject matter contained in Japanese Patent Application No. 9-212776 (filed on Aug. 7, 1997) and Japanese Patent Application No. 9-268293 (filed on Oct. 1, 1997), which are expressly incorporated herein by reference in their entireties.

1. Field of the Invention

The present invention relates to a wire loop type instrument for an endoscope, such as a high-frequency snare. The present invention also relates to a method of producing such a wire loop type instrument.

2. Description of the Prior Art

A wire loop type instrument for an endoscope, e.g. a high-frequency snare, is generally arranged as shown in FIG. 1. An elastic wire 10 is formed from a stranded wire. The elastic wire 10 is bent into a U-shape at the distal end thereof and expanded in a loop shape at the rear of the U-shaped bent portion. When withdrawn into the distal end of a sheath 20, the elastic wire 10 is folded. When projecting from the distal end of the sheath 20, the elastic wire 10 expands in the loop shape by its own elasticity.

An example of the elastic wire 10 which has heretofore been widely used in such a wire loop type instrument includes a 1×7 stranded wire formed by twisting together seven strands 11 of stainless steel. Each strand 11 has a circular cross-sectional configuration with a diameter of the order of from 0.1 mm to 0.15 mm, as shown in FIG. 10.

In addition to the 1×7 stranded wire, various stranded wires are commonly used. Examples include a 1×3 stranded wire formed by twisting together three strands, a 1×19 stranded wire having 19 strands twisted together, and a 1×37 stranded wire containing 37 twisted strands.

FIG. 11 shows elastic wire 10 formed from a 1×7 stranded wire. When this wire is bent into a U-shape as shown by the chain double-dashed line, each strand 11 is loosened and irregularly deformed as shown in FIG. 12. Consequently, the arrangement of the strands 11 is disordered As a result, the bent portion of the elastic wire 10 swells, and the wire 10 may become impossible to withdraw into the sheath 20. In actual use, the bent portion may be readily broken by the stress concentration or Joule's heat generated by the high-frequency electric current when a polyp or the like is pinched tight with the elastic wire 10. Moreover, the deformed elastic wire 10 locks inferior, causing the commercial value of the wire loop type instrument to be lowered.

SUMMARY OF THE INVENTION

An object of the present invention is to provide a wire loop type instrument for an endoscope that is designed so that an elastic wire can be smoothly bent into a U-shape at the distal end of the loop without causing the strands to loosen.

Another object of the present invention is to provide a method of producing such a wire loop type instrument for an endoscope.

Other objects and advantages of the present invention will become apparent from the following detailed description of illustrated embodiments of the invention.

According to the present invention, there is provided a wire loop type instrument for an endoscope. The instrument has an elastic wire formed from a stranded wire. The elastic wire is bent into a U-shape at a portion thereof and expanded in a loop shape at the rear of the U-shaped bent portion. When withdrawn into the distal end of a sheath, the elastic wire is folded. When projecting from the distal end of the sheath, the elastic wire expands in the loop shape by its own elasticity. Each strand of the stranded wire forming the elastic wire has a non-circular cross-sectional configuration in which the strand is more resistant to bending in other directions than in a direction toward the center of the elastic wire.

In addition, there is provided a method of producing a wire loop type instrument for an endoscope which has an elastic wire formed from a stranded wire. The elastic wire is bent into a U-shape at a portion thereof and expanded in a loop shape at the rear of the U-shaped bent portion. When withdrawn into the distal end of a sheath, the elastic wire is folded. When projecting from the distal end of the sheath, the elastic wire expands in the loop shape by its own elasticity. The stranded wire is formed by twisting together a plurality of strands each having a circular cross-sectional configuration. The stranded wire is passed through a die provided with a hole having a smaller diameter than that of the stranded wire, thereby compression-deforming each of the strands into a non-circular cross-sectional configuration.

In addition, there is provided a wire loop type instrument for an endoscope. The instrument has an elastic wire bent into a U-shape at a portion thereof and expanded in a loop shape at the rear of the U-shaped bent portion. When withdrawn into the distal end of a sheath, the elastic wire is folded. When projecting from the distal end of the sheath, the elastic wire expands in the loop shape by its own elasticity. As the elastic wire, a composite stranded wire is used which is formed by twisting together a plurality of stranded wires each formed from a plurality of strands twisted together.

BRIEF DESCRIPTION OF THE DRAWINGS

The present invention may be more fully understood from the description of preferred embodiments of the invention set forth below, together with the accompanying drawings, in which:

FIG. 7 is a sectional front view of a composite stranded wire forming an elastic wire according to a fourth embodiment of the present invention;

FIG. 8 is a sectional front view of a composite stranded wire forming an elastic wire according to a fifth embodiment of the present invention;

FIG. 9 is a sectional front view of a composite stranded wire forming an elastic wire according to a sixth embodiment of the present invention;

FIG. 10 is a sectional view of an elastic wire used in a conventional wire loop type instrument for an endoscope, taken in a direction perpendicular to the axis of the wire;

DESCRIPTION OF THE EMBODIMENTS

Embodiments of the present invention will be described below with reference to the accompanying drawings.

Figure 1:
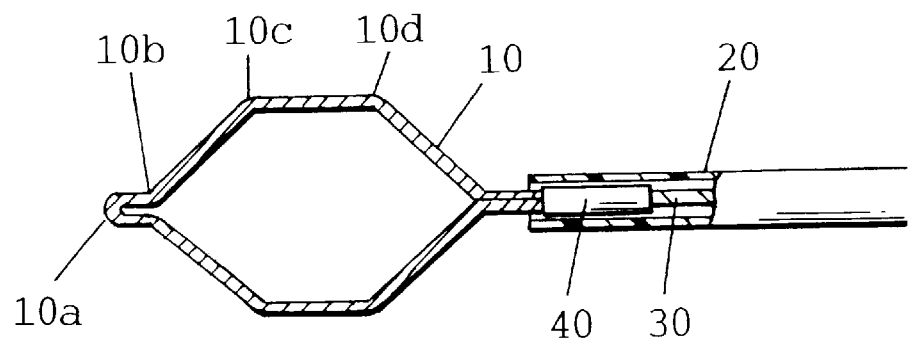
FIG. 1 is a sectional side view of the distal end portion of a wire loop type instrument for an endoscope.

FIG. 1 shows the distal end portion of a high-frequency snare for an endoscope that is used to remove a polyp. It should, however, be noted that the present invention is not necessarily limited to high-frequency snares but can be applied to various wire loop type instruments for endoscopes that need to bend an elastic wire into a U-shape with a small radius of curvature at the distal end thereof.

Referring to FIG. 1, a flexible sheath 20 is formed from a tube of a resin material, for example, tetrafluoroethylene resin. The sheath 20 is removably inserted into an instrument-inserting channel of an endoscope (not shown).

An electrically conductive control wire 30 is axially movably inserted in the sheath 20. The movement of the control wire 30 is controlled at a control part (not shown) that is connected to the proximal end of the sheath 20.

An elastic wire 10 is connected through a connecting pipe 40 to the distal end of the control wire 30. The elastic wire 10 is formed so as to assume a predetermined loop shape under natural conditions. The proximal end of the elastic wire 10 is inserted into the front end of the connecting pipe 40 and secured by silver brazing. The distal end of the control wire 30 is inserted into the rear end of the connecting pipe 40 and secured by silver brazing.

The elastic wire 10 is a single stranded wire of stainless steel. The elastic wire 10 is bent into a U-shape to form a U-shaped bent end portion 10a. The elastic wire 10 is further bent to form a loop at the rear of the U-shaped bent portion 10a.

Consequently, when projecting from the distal end of the sheath 20, the elastic wire 10 expands in a loop shape by its own elasticity. When pulled backward (toward the control part) with the control wire 30, the elastic wire 10 is withdrawn into the sheath 20 and thus folded.

In this embodiment, each section of the elastic wire 10 that extends rearward from the U-shaped bent portion 10a is bent at three bent portions 10b, 10c and 10d. However, it should be noted that the number of bent portions may be different from three. Alternatively, the sections of the elastic wire 10 that form a loop may be smoothly curved instead of being bent angularly.

In this embodiment, a 1×7 stranded wire is used as the elastic wire 10. The stranded wire is formed by twisting together seven strands 11 of stainless steel having a circular cross-section with a diameter of the order of 0.1 mm to 0.2 mm. The seven strands 11 have the same diameter. One strand 11 is disposed in the center to extend straight, and the other six strands 11 are helically wound around the central strand 11.

However, in the elastic wire 10 according to the present invention, such a stranded wire is not used as it is, but it is subjected to swaging. That is, the stranded wire is passed through a die provided with a hole having a smaller diameter than that of the stranded wire, thereby compression-deforming each strand 11.

Figure 2:
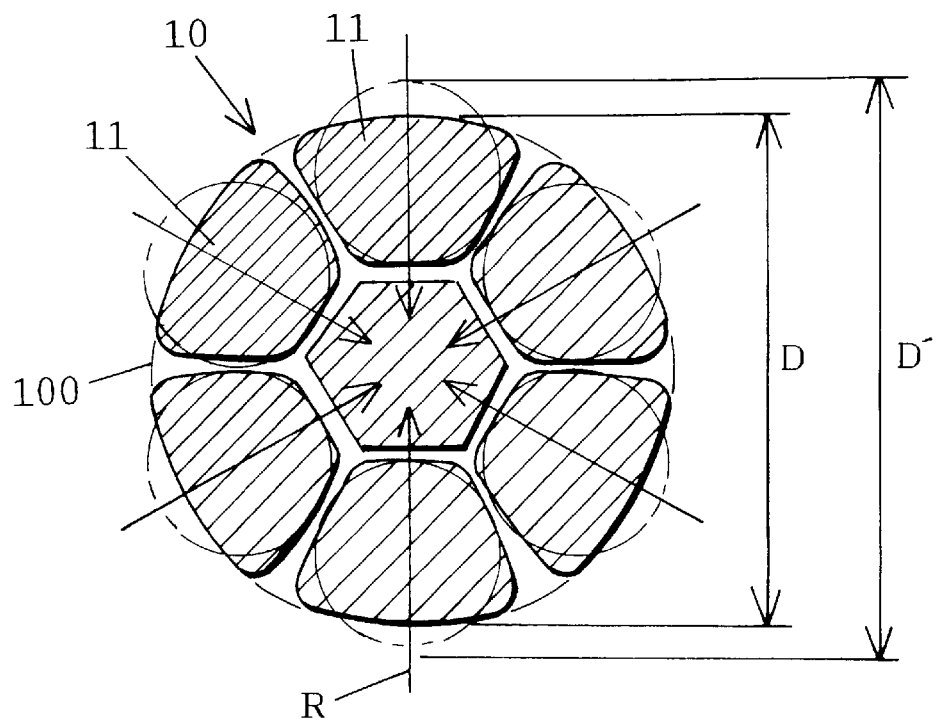
FIG. 2 is a sectional view of an elastic wire according to a first embodiment of the present invention, taken in a direction perpendicular to the axis of the wire.

Thus, as shown in FIG. 2, the elastic wire 10 is plastically deformed such that the gap between the strands 11 disappears. As a result, among the seven strands 11, the central strand 11 has a hexagonal cross-sectional configuration, and the six strands 11 twisted around the central strand 11 each have a cross-sectional configuration close to a trapezoid. The portion of each peripheral strand 11 that corresponds to the base of the trapezoid lies on the outer surface side of the elastic wire 10, and the sides (slanting sides) of each pair of adjacent trapezoidal strands 11 face each other. Reference numeral 100 denotes the hole in the die.

The result of an experiment reveals that the degree of change in the diameter of the elastic wire 10 by the swaging process is preferably within the range of from $(D'-D)/D' = 0.08$ to $0.105$. In the expression, D' is the diameter of the elastic wire 10 before swaging, and D is the diameter of the wire 10 after swaging (that is, the diameter of the hole 100 in the die). When the diameter of each strand 11 is from 0.1 mm to 0.2 mm, the diameter of the elastic wire 10 after swaging is in the range of from 0.276 mm to 0.552 mm.

Figure 3:
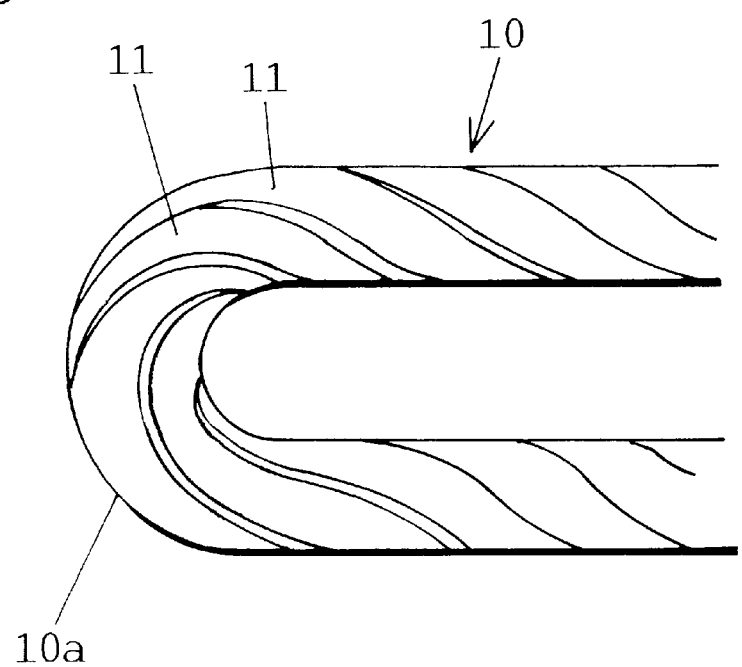
FIG. 3 is a side view of a U-shaped bent portion of the elastic wire according to the first embodiment of the present invention.

As shown in FIG. 3, even when it is bent into a U-shape with a small radius of curvature, the elastic wire 10 subjected to the swaging process maintains a very smooth condition without the strands 11 getting loose.

The reason why the elastic wire 10 can be favorably bent without causing the strands 11 to loosen may be as follows. As shown in FIG. 2, each strand 11 is formed into a shape close to a trapezoid in which a portion thereof that corresponds to the base of the trapezoid lies on the outer surface side of the elastic wire 10. Consequently, each strand 11 is more resistant to bending in other directions than in the direction R toward the center of the stranded wire, which forms the elastic wire 10. Therefore, when the elastic wire 10 is bent into a U-shape, each strand 11 does not move in a direction in which it untwists.

Figure 4:
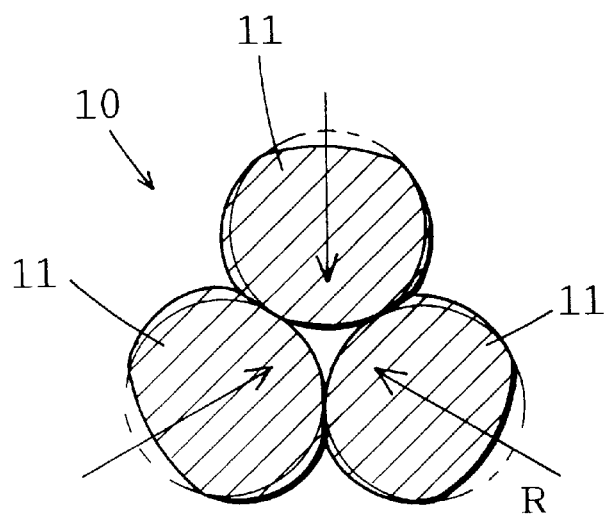
FIG. 4 is a sectional view of an elastic wire according to a second embodiment of the present invention, taken in a direction perpendicular to the axis of the wire.

It should be noted that the elastic wire 10 is not necessarily limited to the 1×7 stranded wire, and that various other stranded wires may be used, for example, a 1×3 stranded wire such as that shown in FIG. 4. In such a case also, by swaging the stranded wire, each strand 11 has such a cross-sectional configuration that the strand 11 is more resistant to bending in other directions than in the direction R toward the center of the elastic wire 10.

The elastic wire 10 according to the present invention does not always need to be subjected to swaging. The elastic wire 10 may be formed by twisting together strands 11 having a non-circular cross-sectional configuration in which each strand 11 is more resistant to bending in other directions than in the direction toward the center of the elastic wire 10.

According to the present invention, an elastic wire is formed from a stranded wire formed by twisting together strands each having a non-circular cross-sectional configuration in which each strand is more resistant to bending in other directions than in the direction toward the center of the stranded wire. Accordingly, the elastic wire can be smoothly bent into a U-shape with a small radius of curvature at the distal end of the loop without causing the strands to loosen. Therefore, there is no likelihood of the elastic wire becoming difficult to withdraw into the sheath, and there will be no failure of mechanical strength of the elastic wire during use. Furthermore, the elastic wire looks superior in quality, and thus a wire loop type instrument of great commercial value can be formed.

Figure 5:
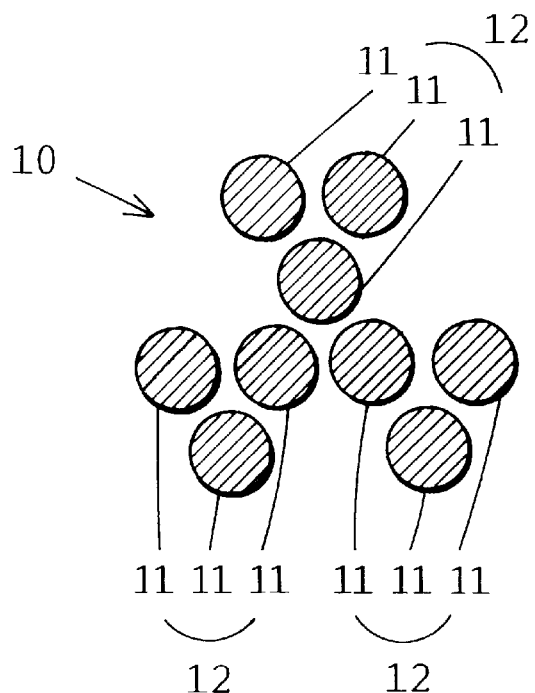
FIG. 5 is a sectional front view of a composite stranded wire forming an elastic wire according to a third embodiment of the present invention.

According to a third embodiment of the present invention, a composite stranded wire is used as the elastic wire 10. As shown in the sectional view of FIG. 5, the composite stranded wire is formed by twisting together a plurality of stranded wires 12 each formed by twisting together a plurality of strands 11 of stainless steel, for example.

In this embodiment, each stranded wire 12 is formed by twisting together three strands 11 of the same diameter, and three stranded wires 12 are twisted together to form a 3×3 composite stranded wire as an elastic wire 10.

It should be noted that each stranded wire 12 has the same direction of twist, and the direction of twist of the composite stranded wire is opposite to that of each stranded wire 12. The same is the case with various composite stranded wires described hereinafter.

Figure 6:
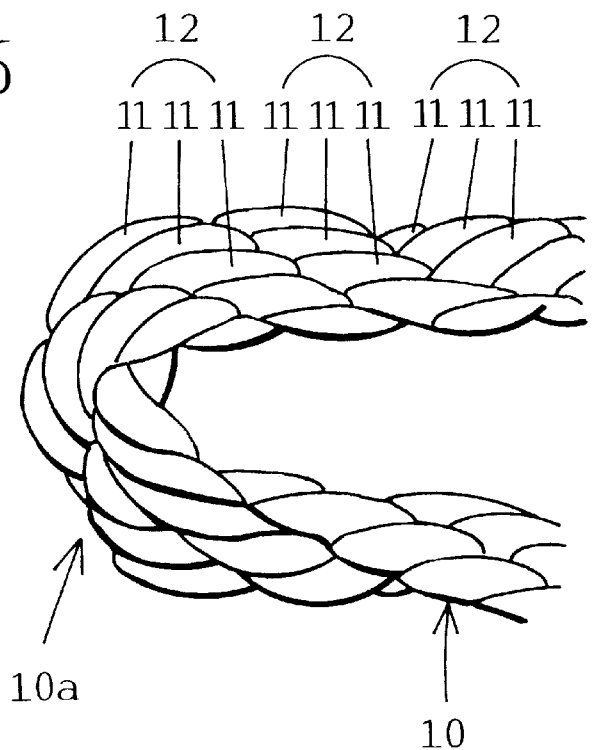
FIG. 6 is a side view of a U-shaped bent portion of the elastic wire according to the third embodiment of the present invention.
Figure 11:
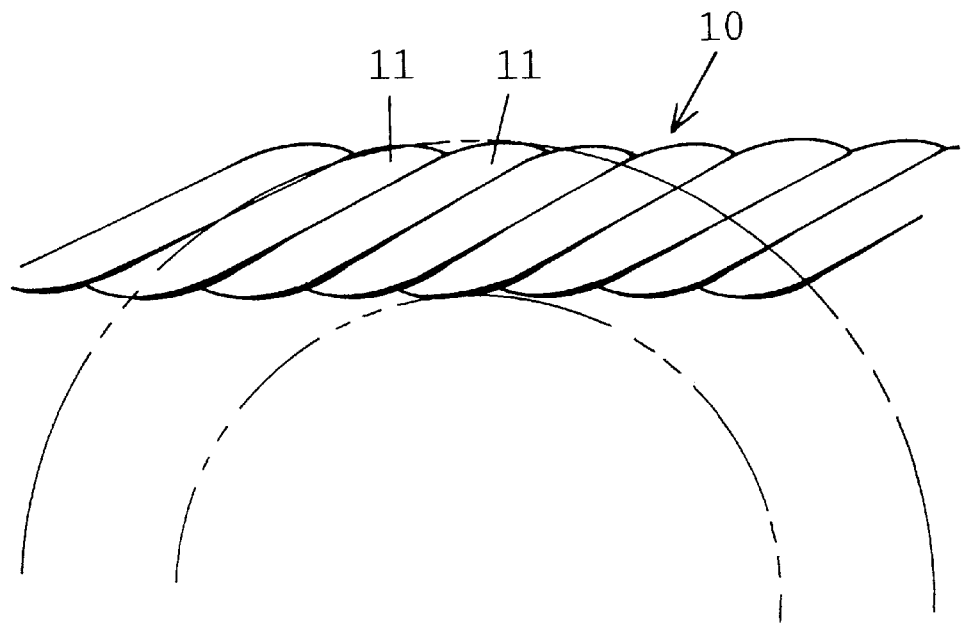
FIG. 11 is a side view of the elastic wire used in the conventional wire loop type instrument.
Figure 12:
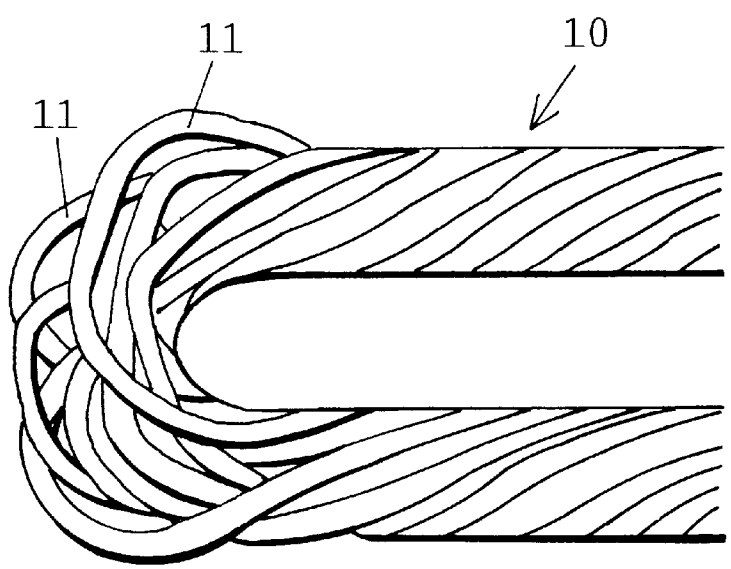
FIG. 12 is a side view of a U-shaped bent portion of the conventional elastic wire.

FIG. 6 is an enlarged view of a bent end portion 10a of an elastic wire 10 formed from such a composite stranded wire. The composite stranded wire is smoothly bent into a U-shape without causing the strands 11 to loosen.

Thus, the use of such a composite stranded wire for the elastic wire 10 enables the elastic wire 10 to be bent into a U-shape as a whole at the bent end portion 10a. At this time, there is little likelihood of the strands 11 loosening because they are complexly interlocked with each other.

Consequently, there is no likelihood that the bent end portion 10a of the elastic wire 10 will swell and make the wire 10 impossible to withdraw into the sheath 20. Further, the bent end portion 10a will not be readily broken by the stress concentration or Joule's heat generated by the high-frequency electric current when a polyp or the like is pinched tight with the elastic wire 10. Thus, it is possible to obtain a wire loop type instrument that looks superior in quality and has great commercial value.

It should be noted that the composite stranded wire that forms the elastic wire 10 is not necessarily limited to the 3×3 stranded wire, but various other composite stranded wires may be used. Examples of the usable composite stranded wires include a 7×3 composite stranded wire such as that shown in FIG. 7, which is formed by twisting together three stranded wires 12 each formed from seven strands 11 twisted together. It is also possible to use a 7×7 composite stranded wire such as that shown in FIG. 8, which is formed by twisting together seven stranded wires 12 each formed from seven strands 11 twisted together. A {(1×3)+(1×7)×5} composite stranded wire such as that shown in FIG. 9 is also usable, which is formed by twisting five (1×7) stranded wires 12 around a 1×3 stranded wire used as an axis.

It should be noted that the diameter of each strand 11 in a composite stranded wire is preferably within the range of from 0.05 mm to 0.15 mm from the viewpoint of the bending habit and mechanical strength of the elastic wire 10.

According to the present invention, an elastic wire that is bent into a U-shape and looped at the rear of the U-shaped bent portion is formed from a composite stranded wire formed by twisting together a plurality of stranded wires each formed from a plurality of strands twisted together. Thus, the elastic wire can be smoothly bent into a U-shape at the distal end of the loop without causing the strands to loosen. Therefore, there is no likelihood of the elastic wire becoming difficult to withdraw into the sheath, and there will be no failure of mechanical strength of the elastic wire during use. Furthermore, the elastic wire looks superior in quality. Thus, it is possible to form a wire loop type instrument of great commercial value.

While the invention has been described by reference to specific embodiments chosen for purposes of illustration, it should be apparent that numerous modifications could be made thereto by those skilled in the art without departing from the basic concept and scope of the invention.

We claim:

1. A wire loop type instrument for an endoscope comprising an elastic wire formed from a stranded wire, said elastic wire being bent into a U-shape at a portion thereof and expanded into a loop shape at a rear of said portion, said elastic wire being provided such that when withdrawn into a distal end of a sheath, said elastic wire is folded, and when projecting from the distal end of said sheath, said elastic wire expands into said loop shape by its own elasticity, wherein each strand of the stranded wire forming said elastic wire has a substantially trapezoidal cross-sectional configuration in which the strand is more resistant to bending in other directions than in a direction toward a center of said elastic wire, and wherein a portion of said strand that corresponds to a base of said trapezoid lies on an outer surface side of said elastic wire, and each pair of adjacent strands face each other at respective portions each corresponding to a slanting side of said trapezoid.

2. A wire loop type instrument according to claim 1, which is a high-frequency snare to remove a polyp.

3. A method of producing a wire loop type instrument for an endoscope which has an elastic wire formed from a stranded wire, said elastic wire being bent into a U-shape at a portion thereof and expanded into a loop shape at a rear of said portion so that when withdrawn into a distal end of a sheath, said elastic wire is folded, and when projecting from the distal end of said sheath, said elastic wire expands into said loop shape by its own elasticity, wherein said stranded wire is formed by twisting together a plurality of stands, each having a circular cross-sectional configuration, and said stranded wire is passed through a die provided with a hole having a smaller diameter than that of said stranded wire, thereby compression-deforming each of said strands into a substantially trapezoidal cross-sectional configuration, and wherein a portion of said strand that corresponds to a base of said trapezoid lies on an outer surface side of said elastic wire, and each pair of adjacent strands face each other at respective portions each corresponding to a slanting side of said trapezoid.

4. A method according to claim 3, wherein the diameter of the hole in said die is smaller than the diameter of said stranded wire before passage through said die by from 8% to 10.5%.

\* \* \* \* \*